United States Patent
Lu et al.

(10) Patent No.: US 8,437,591 B1
(45) Date of Patent: May 7, 2013

(54) REUSABLE BIOCHEMICAL AGENT SENSOR AND METHOD USING OPTICAL MICRO-RESONATOR GRID ARRAYS

(75) Inventors: Ryan P. Lu, San Diego, CA (US); Christopher K. Huynh, Rosemead, CA (US); Ayax D. Ramirez, Chula Vista, CA (US); Joshua M. Kvavle, San Diego, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 91 days.

(21) Appl. No.: 13/165,330

(22) Filed: Jun. 21, 2011

(51) Int. Cl.
*G02B 6/26* (2006.01)

(52) U.S. Cl.
USPC .................. 385/39; 385/27; 385/16; 385/30

(58) Field of Classification Search .................. 385/27, 385/30, 31, 36, 39, 99, 16–20
See application file for complete search history.

(56) References Cited

U.S. PATENT DOCUMENTS

| | | | | |
|---|---|---|---|---|
| 6,393,174 B1* | 5/2002 | Karaguleff et al. | .............. | 385/16 |
| 6,519,382 B1* | 2/2003 | Jurbergs et al. | ................. | 385/18 |
| 6,583,399 B1* | 6/2003 | Hunziker et al. | ......... | 250/214 R |
| 7,444,045 B2* | 10/2008 | Fan et al. | ......................... | 385/27 |
| 7,491,491 B2 | 2/2009 | Arnold et al. | | |
| 8,116,624 B1* | 2/2012 | Wach | ............................... | 398/20 |
| 2002/0044739 A1* | 4/2002 | Vahala et al. | .................... | 385/30 |
| 2004/0137478 A1 | 7/2004 | Arnold et al. | | |
| 2004/0196465 A1* | 10/2004 | Arnold et al. | ................. | 356/432 |
| 2010/0142887 A1* | 6/2010 | Digonnet et al. | .............. | 385/16 |
| 2010/0297363 A1 | 11/2010 | Arnold et al. | | |

OTHER PUBLICATIONS

Vollmer, Frank, Taking Detection to the Limit, B.I.F. Futura, 2005, vol. 20, pp. 239-244.

* cited by examiner

*Primary Examiner* — Ellen Kim
(74) *Attorney, Agent, or Firm* — Ryan J. Friedl; Kyle Eppele

(57) ABSTRACT

A system includes at least two optical fibers crossing to form a vertice. The optical fibers comprise a core, a cladding surrounding the core, and a conductive coating at least partially surrounding the length of the cladding. A portion of the core of each of the fibers is exposed proximate to the vertice. An optical microsphere whispering gallery mode (WGM) resonator is positioned to cover exposed core portion of each fiber and in contact with the conductive coating of each fiber. The optical fibers may be orthogonal to each other or offset by a non-orthogonal and non-zero angle. The WGM resonator may be positioned between each of the fibers. An optical energy source may be coupled to an end of the optical fibers, with an optical detector coupled to the other end. A voltage source may be connected to the conductive coating of each of the optical fibers.

20 Claims, 4 Drawing Sheets

REUSABLE BIOCHEMICAL AGENT SENSOR AND METHOD USING OPTICAL MICRO-RESONATOR GRID ARRAYS

FEDERALLY-SPONSORED RESEARCH AND DEVELOPMENT

The Reusable Biochemical Agent Sensor and Method Using Optical Micro-Resonator Grid Arrays is assigned to the United States Government and is available for licensing for commercial purposes. Licensing and technical inquiries may be directed to the Office of Research and Technical Applications, Space and Naval Warfare Systems Center, Pacific, Code 72120, San Diego, Calif., 92152; voice (619) 553-5118; email ssc_pac_T2@navy.mil; reference Navy Case Number 100816.

BACKGROUND

The need for low-cost photonic devices has stimulated a significant amount of research in silicon photonics. Although silicon photonics is less well-developed as compared to III-V technologies, it has the potential to make a huge impact on the optical communications industry and in many other photonic applications. Silicon is transparent in the standard ITU optical communication bands, which makes silicon the material of choice for passive and active optoelectronic devices.

Microspheres have been gaining an important place in the optical micro-cavity resonator community due to their high quality factor morphology-dependent resonances (MDRs). Silicon microspheres with high quality factors MDRs are used for resonant detection and filtering of light in the near infrared. The light is coupled to the silicon microsphere with optical fiber half couplers in the near-IR. The observed MDRs have quality factors of 100,000. The experimentally measured quality factors are limited by the sensitivity of the experimental setup; however, the microsphere quality factor is several magnitudes of order higher than current micro-ring resonators.

These optical resonances provide the necessary narrow line width that is needed for high-resolution optical filtering applications, Raman lasers, modulators, and CMOS-compatible detectors in the near-IR. The silicon microsphere shows promise as a building block for silicon micro-photonics, a complementary technology to the already well established CMOS microelectronics technology, for the realization of future micro-electro-photonic integration. Numerous potential applications have been realized by using microspheres, such as: micro-lasers, channel dropping filters, optical switching, ultrafine sensing, displacement measurement, rotation detection, high-resolution spectroscopy, and Raman lasers.

Biochemical warfare has led to the need for early warning devices which can alert the warfighter of impending biochemical threats. A need exists for a reliable and reusable compact system, such as a microsphere-based system, that can detect the presence of biochemical agents with low false positive results.

DETAILED DESCRIPTION OF SOME EMBODIMENTS

Figure 1:
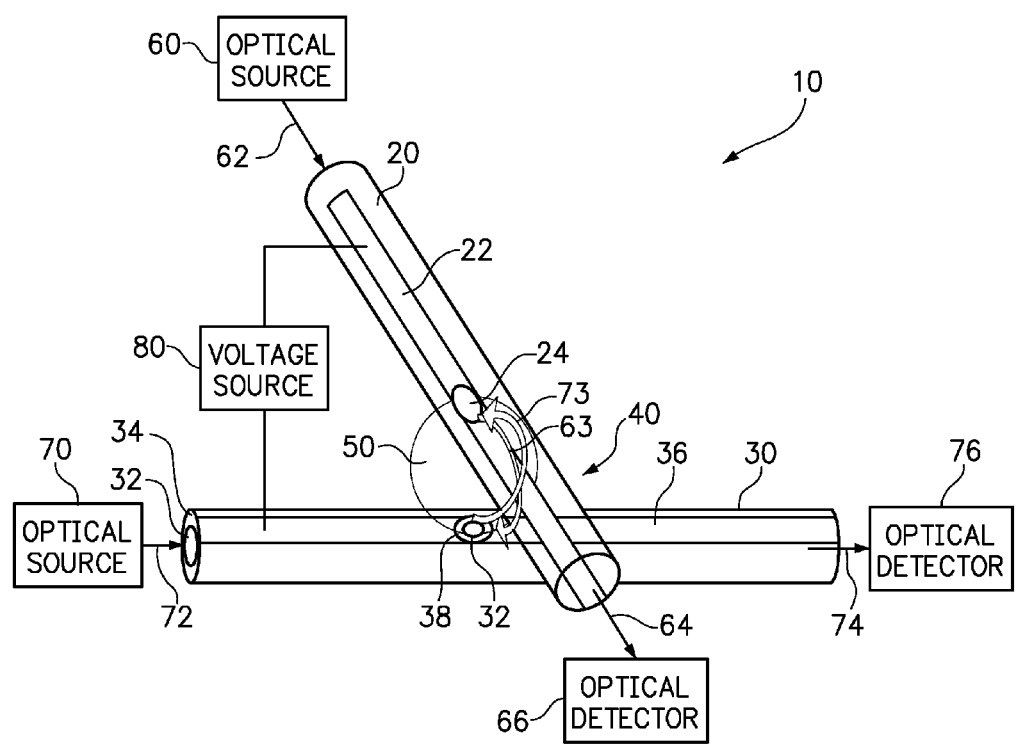
FIG. 1 shows a top perspective view of an embodiment of a system in accordance with the Reusable Biochemical Agent Sensor and Method Using Optical Micro-Resonator Grid Arrays.

FIG. 1 shows a top perspective view of an embodiment of a system 10 in accordance with the Reusable Biochemical Agent Sensor and Method Using Optical Micro-Resonator Grid Arrays. System 10 provides a reusable compact system with near single molecule sensitivity that detects the presence of biochemical agents with low false positive results. System 10 includes at least two optical fibers, fibers 20 and 30, crossing to form a vertice 40. As shown, optical fibers 20 and 30 are orthogonal to each other. In some embodiments, optical fibers 20 and 30 may be differently oriented, such as by being offset from each other by a non-orthogonal and non-zero angle. The offset or orthogonally positioned optical fibers allow optical signals from both optical fibers 20 and 30 to be coupled into the same optical microsphere whispering gallery mode (WGM) resonator 50. This serves to add a level of redundancy to reduce the false positive rate of target analyte detection.

Optical fibers 20 and 30 comprise a core (shown in optical fiber 30 as reference 32), a cladding surrounding the core (shown in optical fiber 30 as reference 34), and a conductive coating (shown in optical fiber 20 as reference 22 and optical fiber 30 as reference 36) at least partially surrounding the length of the cladding. Conductive coatings 22 and 36 are highly conductive and may comprise materials such as a pure metal, composite metal, or conductive polymer. In some embodiments, conductive coatings 22 and 36 may completely surround optical fibers 20 and 30, respectively.

A portion of the core of each of the two optical fibers is exposed proximate to vertice 40. As shown in FIG. 1, optical fiber 20 contains a portion 24 where its cladding is eroded and its core (not shown) is exposed and optical fiber 30 contains a portion 38 where its cladding 34 is eroded and its core 32 is exposed. As an example, the cladding of optical fibers 20 and 30 may be eroded by mechanical polishing, chemical etching, tapering, or laser drilling.

A WGM resonator 50 is positioned to cover the exposed core portion of each of optical fibers 20 and 30. Thus, WGM resonator 50 is positioned over portion 38 of optical fiber 30 and underneath portion 24 of optical fiber 20. In other embodiments, WGM resonator 50 may be positioned over both optical fibers, underneath both optical fibers, or on the side of one or both optical fibers, depending upon the location of WGM resonator 50. For example, if optical fiber 20 is positioned directly on top of optical fiber 30, rather than separated by WGM resonator 50, WGM resonator 50 may rest on top of the exposed core portions of one optical fiber and on the side of the exposed core portion of the other optical fiber. In other embodiments, optical fibers may be parallel and may not create a vertice, with WGM resonator positioned between each optical fiber.

The positioning of WGM resonator 50 in relation to the exposed core portions 24 and 38 allows the surface of the WGM resonator 50 to be within the coupling distance of the evanescent field emanating from the exposed fiber core (such as core 32). In such position, WGM resonator 50 is in contact with the conductive coating of each of optical fibers 20 and 30. Thus, WGM resonator 50 is positioned to be in contact with conductive coating 22 of optical fiber 20 and conductive coating 36 of optical fiber 30.

As shown, WGM resonator 50 is positioned such that it is "sandwiched" between each of the two optical fibers 20 and 30. In such a position, WGM resonator 50 rests on top of optical fiber 30 and optical fiber 20 rests on top of WGM resonator 50. However, other configurations are possible, provided WGM resonator 50 is positioned in relation to the exposed core portions 24 and 38 of optical fibers 20 and 30 proximate to the vertice 40. For example, in some embodiments optical fibers 20 and 30 may contact one another to create a vertice 40. In such an embodiment, WGM 50 may be positioned at one of the four ninety-degree angles formed by the crossing of optical fibers 20 and 30 where WGM 50 contacts both optical fibers 20 and 30. Further, in some embodiments, the surface of WGM 50 may be simultaneously coupled to more than two optical fibers to provide additional functionality.

WGM resonator 50 may comprise a material such as a doped group IV semiconductor, such as silicon or germanium, a doped group III-V compound semiconductor, such as GaAs, InP, GaN, and AlN, and a doped group II-VI compound semiconductor, such as ZnSe and SdSe. WGM resonator 50 may also comprise other compounds such as SiN and amorphous silica. Polymer microspheres, such as polystyrene, may also be utilized. The surface of WGM resonator 50 is functionalized by coating the surface area with a liquid polymer such that only certain biochemical agents can attach to its surface and a shift in its optical resonant frequency is detected and registered.

An optical energy source, such as a tunable laser or broadband light source, may be operatively coupled to one end of each of the two optical fibers, while an optical detector may be operatively coupled to the other end of each of the two optical fibers. As shown, optical source 60 is operatively coupled to optical fiber 20 and provides an optical signal 62 into optical fiber 20. Similarly, optical source 70 is operatively coupled to optical fiber 30 and provides an optical signal 72 into optical fiber 30. WGM resonator 50 causes a portion of optical signal 62 to couple into optical fiber 30, as shown by arrow 63, as well as a portion of optical signal 72 to couple into optical fiber 20, as shown by arrow 73. The resulting signal 64 from optical fiber 20 is output to optical detector 66, while the resulting signal 74 from optical fiber 30 is output to optical detector 76.

Optical detectors 66 and 76 will detect periodic drops in power at frequencies determined by the free spectral range of WGM resonator 50. Changes in the surface chemistry of WGM resonator 50 due to attachment of analytes will result a frequency shift of the periodic power dips. The delta can then be measured and correlated to the concentration of analytes attached to the surface of WGM resonator 50.

A voltage source 80 may be connected to the conductive coating of one or both of optical fibers 20 and 30. Voltage source 80 may be either a direct current (DC) voltage source or an alternating current (AC) voltage source. In some embodiments, separate AC and DC voltage sources may be connected to each of conductive coating 22 of optical fiber 20 and conductive coating 36 of optical fiber 30. Voltage source 80 helps to remove an analyte that has attached to the functionalized surface of WGM resonator 50. Normally, once an analyte attaches to the surface of WGM resonator 50, it is very difficult to remove the analyte. By applying a sufficiently large DC voltage between the opposing optical fibers, an electric current will flow and WGM resonator 50 will heat up due to the microsphere acting as a large impedance. The heat produced is proportional to the square of the current multiplied by the resistance.

In a second embodiment, an AC voltage may be applied which will cause WGM resonator 50 to expand and contract rapidly due to heating and cooling. In a third embodiment, a technique utilizing both heating and vibrating alternately may be used. The application of heat and/or vibrations will provide the energy required to break the bonds between the analyte and the functionalized surface of WGM resonator. This will result in desorption of the analytes from the microsphere surface, which can then be swept away with a fluid, gas or vacuum.

Figure 2:
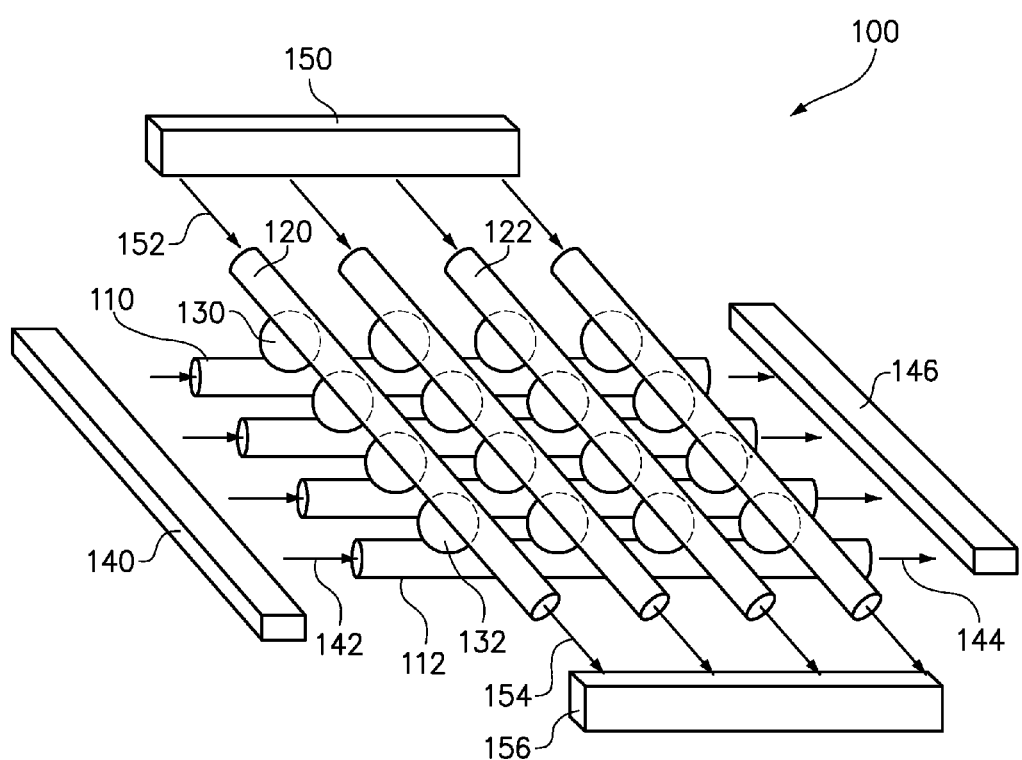
FIG. 2 shows a top perspective view of an embodiment a system configured as a fiber optic grid array, in accordance with the Reusable Biochemical Agent Sensor and Method Using Optical Micro-Resonator Grid Arrays.

FIG. 2 shows a top perspective view of an embodiment a system 100 in accordance with the Reusable Biochemical Agent Sensor and Method Using Optical Micro-Resonator Grid Arrays. System 100 includes more than one optical fibers 110 and 112 oriented in a first direction and more than one optical fibers 120 and 122 oriented in a second direction, with the first direction and second direction being non-parallel. The optical fibers are oriented as a fiber optic grid array, having equal spacing between each successive optical fiber. However, it should be recognized that the spacing of the fibers may vary. For example, in some embodiments, the spacing between optical fibers oriented in one direction may vary. In other embodiments, the spacing between optical fibers oriented in one direction may differ from the spacing between optical fibers oriented in another direction.

At the crossings of each optical fiber, the vertice, a WGM resonator, such as resonators 130 and 132, are positioned between the crossing optical fibers. For example, WGM resonator 130 is positioned on top of optical fiber 110 and below optical fiber 120. It should be noted that not every vertice must contain a WGM resonator located proximate thereto, as design factors may dictate otherwise. Optical fibers 110, 112, 120, and 122 are configured similarly to optical fibers 20 and 30 of FIG. 1, including a core, cladding, conductive coating, and exposed core portion (not shown). Each WGM resonator is positioned to cover the exposed core portion of, and in contact with the conductive coating of, each of optical fiber forming the vertice. For example, WGM resonator 132 is positioned over the exposed core portion of optical fiber 112 and positioned below the exposed core portion of optical fiber 120. Further, the conductive coating (not shown) of optical fibers 112 and 120 is in contact with WGM resonator 132.

System 100 further includes optical energy sources 140 and 150 and optical detectors 146 and 156 operatively coupled to the fiber optic grid array. Optical energy source 140 is configured to provide optical signals 142 to optical fibers oriented in a first direction, which are output as signals 144 to optical detector 146. Optical energy source 150 is configured to provide optical signals 152 to optical fibers oriented in a second direction, which are output as signals 154 to optical detector 156. One optical energy source providing signals to multiple fibers helps to reduce the device power requirements and device cost.

In some embodiments, optical energy sources 140 and 150 are configured to provide the same optical signal to each optical fiber. In some embodiments, optical energy sources 140 and 150 are configured to provide different optical signals to one or more of the optical fibers they are operatively coupled to. Such a configuration, along with the ability to use a particularly configured WGM resonator, allows for detection of multiple target analytes using the same system 100. As shown in FIG. 2, there are four rows of WGM resonators 130 and 132. Each row may include a WGM resonator comprised of a different material. Further, for each specific row, a different optical energy signal 142 may be coupled into optical fibers 110 and 112 from optical energy source 140. To add a further layer of differentiation in target analyte detection, a different optical energy signal 152 may be coupled into the optical fibers 120 and 122 from optical energy source 150.

As an example, to detect a negatively charged protein such as bovine serum albumin a WGM resonator surface coating comprised of oligonucleotides such as aminosilane (for positively charged amino groups) producing $10^{12}$-$10^{13}$ cm$^2$ binding sites and an optical signal of 1340 nm may be used. As another example, multiple surface coatings may be applied. Adsorbing hydrogels such as biotiynylated dextran can be applied as the first coating before applying the molecules of interest.

Figure 3:
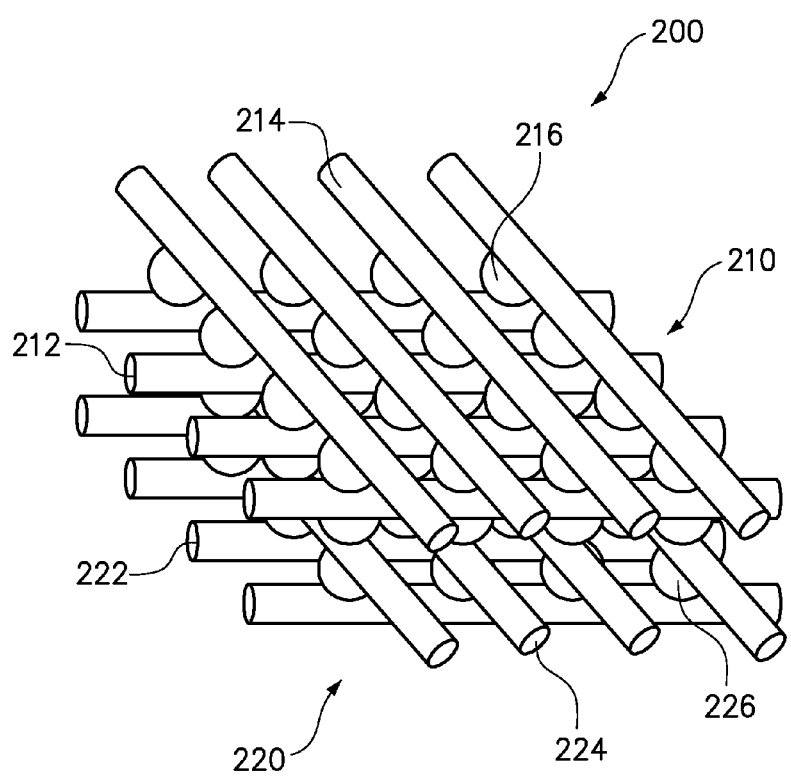
FIG. 3 shows a top perspective view of an embodiment a system configured as a multi-layered fiber optic grid array, in accordance with the Reusable Biochemical Agent Sensor and Method Using Optical Micro-Resonator Grid Arrays.

FIG. 3 shows a top perspective view of an embodiment a system 200 configured as a multi-layered fiber optic grid array, in accordance with the Reusable Biochemical Agent Sensor and Method Using Optical Micro-Resonator Grid Arrays. System 200 represents a stacked version of system 100 of FIG. 2, with similar elements having similar configurations. System 200 includes a first fiber optic grid array layer 210 and a second fiber optic grid array layer 220. First grid array layer 210 includes optical fibers 212 oriented in a first direction, optical fibers 214 oriented in a second direction, and a WGM resonator 216 positioned at each vertice between optical fibers 212 and 214 to cover the exposed core portions of optical fibers 212 and 214 (not shown). Second grid array layer 220 includes optical fibers 222 oriented in a first direction, optical fibers 224 oriented in a second direction, and a WGM resonator 226 positioned at each vertice between optical fibers 222 and 224 to cover the exposed core portions of optical fibers 222 and 224 (not shown). It should be noted that not every vertice must contain a WGM resonator located proximate thereto, as design factors may dictate otherwise.

System 200 may further include optical energy sources and optical detectors (not shown) operatively coupled to the input and output, respectively, of each optical fiber. In some embodiments, a separate optical energy source will be operatively coupled to each optical fiber oriented in the same direction. In other embodiments, separate optical energy sources may be operatively coupled to each individual fiber. Further, a voltage source may be similarly coupled to the conductive coatings (not shown) of each optical fiber.

Figure 4:
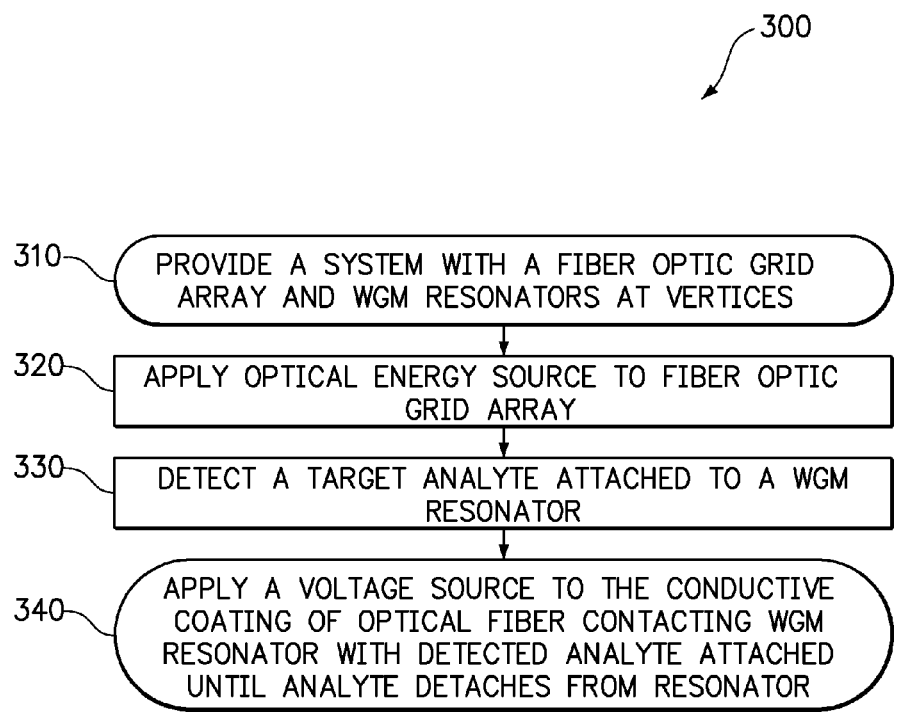
FIG. 4 shows a flowchart of an embodiment of a method in accordance with the Reusable Biochemical Agent Sensor and Method Using Optical Micro-Resonator Grid Arrays.

FIG. 4 shows a flowchart of an embodiment of a method 300 in accordance with the Reusable Biochemical Agent Sensor and Method Using Optical Micro-Resonator Grid Arrays. For illustrative purposes, method 300 will be discussed with reference to system 100. Method 300 may begin at step 310, which involves providing a system 100 with a fiber optic grid array and WGM resonators, such as WGM resonators 130 and 132, at the vertices. Step 320 then involves applying an optical energy source 140 to the optical fiber grid array. In some embodiments, step 320 includes applying a separate optical energy source to each optical fiber of the optical fiber grid array. In some embodiments, step 320 includes applying a separate optical energy source to each group of optical fibers of the optical fiber grid array that are oriented in the same direction.

Next, step 330 involves detecting a target analyte attached to at least one of the optical microsphere WGM resonators, such as WGM resonators 130 or 132, via optical detector 150. A target analyte will attach to one of the WGM resonators by bonding with an oppositely charged protein or polymer. Method 300 may then proceed to step 340, where a voltage is applied to the conductive coating of at least one of the two optical fibers contacting the optical microsphere WGM resonator with the attached target analyte until the target analyte detaches from the optical microsphere WGM resonator. Step 340 serves to "clean" the fiber optic grid array so that additional target analytes may be detected. In some embodiments, step 340 includes applying a DC voltage. In some embodiments, step 340 includes applying an AC voltage. In some embodiments, step 340 includes applying both an AC and a DC voltage. As an example, an pulsed DC voltage applied for a few seconds can achieve a temperature of 300 to 400 Celsius, and will remove a *Bacillus anthracis* (a pathogen of Anthrax) that is attached to a WGM resonator comprised of a mixed self-assembled monolayer (SAM) of 11-mercaptoundecanoic acid (11-MUA) and 6-mercaptohexan-1-ol (6-MHO), followed by a layer of Protein A, and a subsequent layer of monoclonal antibodies (mAb). Removal of the analyte, which may have been pyrolyzed at the high temperatures, can be ensured by flushing with a liquid such as methanol or distilled water.

Many modifications and variations of the Reusable Biochemical Agent Sensor and Method Using Optical Micro-Resonator Grid Arrays are possible in light of the above description. Within the scope of the appended claims, the embodiments of the systems and method described herein may be practiced otherwise than as specifically described. The scope of the claims is not limited to the implementations and the embodiments disclosed herein, but extends to other implementations and embodiments as may be contemplated by those having ordinary skill in the art.

We claim:

1. A system comprising:
    at least two optical fibers crossing to form a vertex, the optical fibers comprising a core, a cladding surrounding the core, and a conductive coating at least partially surrounding the length of the cladding, wherein a portion of the core of each of the two optical fibers is exposed proximate to the vertex; and
    an optical microsphere whispering gallery mode (WGM) resonator covering the exposed core portion of each of the two optical fibers and in contact with the conductive coating of each of the two optical fibers.

2. The system of claim 1, wherein the optical microsphere WGM resonator comprises a material selected from the group consisting of doped group IV semiconductors, doped group III-V compound semiconductors, and doped group II-VI compound semiconductors.

3. The system of claim 1 further comprising an optical energy source operatively coupled to one end of each of the two optical fibers.

4. The system of claim 3 further comprising an optical detector operatively coupled to the other end of each of the two optical fibers.

5. The system of claim 1 wherein the conductive coating comprises a conductive polymer.

6. The system of claim 1 wherein the conductive coating comprises a metal.

7. The system of claim 1 further comprising a direct current voltage source connected to the conductive coating of at least one of the two optical fibers.

8. The system of claim 1 further comprising an alternating current voltage source connected to the conductive coating of at least one of the two optical fibers.

9. The system of claim 1, wherein the at least two optical fibers are orthogonal to each other.

10. The system of claim 1, wherein the at least two optical fibers are offset from each other by a non-orthogonal and non-zero angle.

11. The system of claim 1, wherein the optical microsphere WGM resonator is positioned between each of the two optical fibers.

12. A system comprising:
at least one optical fiber grid array comprising a plurality of vertices, each vertex of the plurality of vertices formed by at least two optical fibers, each of the two optical fibers comprising a core, a cladding surrounding the core, and a conductive coating at least partially surrounding the length of the cladding, wherein a portion of the core of each of the two optical fibers is exposed proximate to each vertex; and
an optical microsphere whispering gallery mode (WGM) resonator positioned at each vertex covering the exposed core portion of each of the two optical fibers and in contact with the conductive coating of each of the two optical fibers.

13. The system of claim 12, wherein each of the optical microsphere WGM resonators are positioned between each of the two optical fibers.

14. The system of claim 12 further comprising:
an optical energy source operatively coupled to one end of at least one of the two optical fibers;
an optical detector operatively coupled to the other end of the at least one the two optical fibers; and
a voltage source connected to the conductive coating of the at least one of the two optical fibers.

15. A method comprising the steps of:
providing a system comprising
at least one optical fiber grid array comprising a plurality of vertices, each vertex of the plurality of vertices formed by at least two optical fibers, each of the two optical fibers comprising a core, a cladding surrounding the core, and a conductive coating at least partially surrounding the length of the cladding, wherein a portion of the core of each of the two optical fibers is exposed proximate to each vertex, and
an optical microsphere whispering gallery mode (WGM) resonator positioned at each vertex covering the core portion of each of the two optical fibers and in contact with the conductive coating of each of the two optical fibers;
applying an optical energy source to the optical fiber grid array;
detecting a target analyte attached to at least one of the optical microsphere WGM resonators; and
applying a voltage to the conductive coating of at least one of the two optical fibers contacting the optical microsphere WGM resonator with the attached target analyte until the target analyte detaches from the optical microsphere WGM resonator.

16. The method of claim 15, wherein the step of applying an optical energy source to the optical fiber grid array includes applying a separate optical energy source to each optical fiber of the optical fiber grid array.

17. The method of claim 15, wherein the step of applying an optical energy source to the optical fiber grid array includes applying a separate optical energy source to each group of optical fibers of the optical fiber grid array that are oriented in the same direction.

18. The method of claim 15, wherein the step of applying a voltage to the conductive coating of at least one of the optical fibers includes applying a direct current voltage.

19. The method of claim 15, wherein the step of applying a voltage to the conductive coating of at least one of the optical fibers includes applying an alternating current voltage.

20. The method of claim 15, wherein the step of applying a voltage to the conductive coating of at least one of the optical fibers includes applying both a direct current voltage and an alternating current voltage.

* * * * *